US008445666B2

(12) United States Patent
Rigoutsos et al.

(10) Patent No.: US 8,445,666 B2
(45) Date of Patent: May 21, 2013

(54) RIBONUCLEIC ACID INTERFERENCE MOLECULES

(75) Inventors: Isidore Rigoutsos, Astoria, NY (US); Tien Huynh, Yorktown Heights, NY (US); Kevin Charles Miranda, McDowall (AU)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/283,103

(22) Filed: Oct. 27, 2011

(65) Prior Publication Data

US 2012/0040460 A1    Feb. 16, 2012

Related U.S. Application Data

(62) Division of application No. 11/352,152, filed on Feb. 10, 2006, now abandoned.

(60) Provisional application No. 60/652,499, filed on Feb. 11, 2005.

(51) Int. Cl.
*C07H 2/04* (2006.01)
*C07H 21/02* (2006.01)
*C12N 15/00* (2006.01)

(52) U.S. Cl.
USPC .......................................... 536/24.5; 435/455

(58) Field of Classification Search
None
See application file for complete search history.

(56) References Cited

U.S. PATENT DOCUMENTS

| | | | |
|---|---|---|---|
| 5,474,796 | A | 12/1995 | Brennan |
| 6,108,666 | A | 8/2000 | Floratos et al. |
| 6,812,339 | B1 | 11/2004 | Venter et al. |
| 2006/0263798 | A1 | 11/2006 | Huynh et al. |
| 2007/0154896 | A1 | 7/2007 | Huynh et al. |

OTHER PUBLICATIONS

Hofacker et al. Fast Folding and Comparison of RNA Secondary Structures, Monatshefte fur Chemie (Chemical Monthly), vol. 125, pp. 167-188, 1994.

Mathews et al. Expanded Sequence Dependence of Thermodynamic Parameters Improves Prediction of RNA Secondary Structure, J. Mol. Biol. vol. 228, pp. 911-940, 1999.
Griffiths-Jones et al. Rfam: An RNA Family Database, Nucleic Acids Research, vol. 31, No. 1, pp. 439-441, 2003.
Altschul et al., Basic Local Alignment Search Tool, J. Mol. Biol., vol. 215, pp. 403-410, 1990.
Rigoutsos et al., Combinatorial Pattern Discovery in Biological Sequences: The Teiresias Algorithm, Bioinformatics, vol. 14, No. 1, pp. 55-67, 1998.
Stabenau et al. The Ensemble Core Software Libraries, Genome Research, vol. 14, pp. 929-933, 2004.
Stark et al., Identification of *Drosophila* MicroRNA Targets, PLos Biology, vol. 1, Issue 3, pp. 397-409, 2003.
Rehmsmeier et al., Fast and Effective Prediction of MicroRNA/Target Duplexes, RNA, vol. 10, pp. 1507-1517, 2004.
Enright et al., MicroRNA Targets in *Drosophila*, Genome Biology, vol. 5, Issue 1, Article R1, pp. 1-14, 2003.
Lai et al., Computational Identification of *Drosophilia* MicroRNA Genes, Genome Biology, vol. 4, Issue 7, Article R42, pp. 1-20, 2003.
Lim et al., The MicroRNAs of *Caenorhabditis elegans*, Genes and Development, vol. 17, pp. 991-1008, 2003.
Berezikov et al., Phylogenetic Shadowing and Computational Identification of Human MicroRNA Genes, Cell, vol. 120, pp. 21-24, 2005.
Lim et al., Vertebrate MicroRNA Genes, Science Magazine, vol. 299, p. 1540, Mar. 2003.
Bentwich et al., Identification of Hundreds of Conserved and Nonconserved Human microRNAs, Nature Genetics, vol. 37, No. 7, pp. 766-770, Jul. 2005.
Wootton et al., Statistics of Local Complexity in Amino Acid Sequences and Sequence Databases, Computers and Chemistry, vol. 17, No. 2, pp. 149-163, 1993.
Brazma et al., Approaches to the Automatic Discovery of Patterns in Biosequences, Journal of Computational Biology 5, 279-305 (1998).
Cowan, Expected Frequencies of DNA Patterns using Whittle's Formula, Journal of Applied Probability 28, 886-892 (1991).

*Primary Examiner* — Richard Schnizer
(74) *Attorney, Agent, or Firm* — Ryan, Mason & Lewis, LLP

(57) ABSTRACT

Ribonucleic acid interference molecules are provided. In one aspect of the invention, a method for regulating gene expression comprises the following step. At least one nucleic acid molecule comprising at least one of one or more precursor sequences having SEQ ID NO: 1 through SEQ ID NO: 103, 948, each one of the precursor sequences containing one or more mature sequences having SEQ ID NO: 103,949 through SEQ ID NO: 230,447, is used to regulate the expression of one or more genes.

8 Claims, No Drawings

RIBONUCLEIC ACID INTERFERENCE MOLECULES

CROSS REFERENCE TO RELATED APPLICATIONS

This application is a divisional of U.S. patent application Ser. No. 11/352,152, filed Feb. 10, 2006, which claims the benefit of U.S. Provisional Application No. 60/652,499, filed Feb. 11, 2005, the disclosure of which are incorporated by reference herein.

This application is related to U.S. patent application Ser. No. 11/351,821, entitled "System and Method for Identification of MicroRNA Target Sites and Corresponding Targeting MicroRNA," and to U.S. patent application Ser. No. 11/351,951, entitled "System and Method for Identification of MicroRNA Precursor Sequences and Corresponding Mature MicroRNA Sequences from Genomic Sequences," the disclosures of which are incorporated by reference herein.

FIELD OF THE INVENTION

The present invention relates to genes and, more particularly, to ribonucleic acid interference molecules and their role in gene expression.

BACKGROUND OF THE INVENTION

The ability of an organism to regulate the expression of its genes is of central importance to life. A breakdown in this homeostasis leads to disease states, such as cancer, where a cell multiplies uncontrollably, to the detriment of the organism. The general mechanisms utilized by organisms to maintain this gene expression homeostasis are the focus of intense scientific study.

It recently has been discovered that some cells are able to down-regulate their gene expression through certain ribonucleic acid (RNA) molecules. Namely, RNA molecules can act as potent gene expression regulators either by inducing mRNA degradation or by inhibiting translation; this activity is summarily referred to as post-transcriptional gene silencing or PTGS for short. An alternative name by which it is also known is RNA interference, or RNAi. PTGS/RNAi has been found to function as a mediator of resistance to endogenous and exogenous pathogenic nucleic acids and also as a regulator of the expression of genes inside cells.

The term 'gene expression,' as used herein, refers generally to the transcription of messenger-RNA (mRNA) from a gene, and its subsequent translation into a functional protein. One class of RNA molecules involved in gene expression regulation comprises microRNAs, which are endogenously encoded and regulate gene expression by either disrupting the translation processes or by degrading mRNA transcripts, e.g., inducing post-transcriptional repression of one or more target sequences.

The RNAi/PTGS mechanism allows an organism to employ short RNA sequences to either degrade or disrupt translation of complementary mRNA transcripts. Early studies suggested only a limited role for RNAi, that of a defense mechanism against pathogens. However, the subsequent discovery of many endogenously-encoded microRNAs pointed towards the possibility of this being a more general, in nature, control mechanism. Recent evidence has led the community to hypothesize that a wider spectrum of biological processes are affected by RNAi, thus extending the range of this presumed control layer.

A better understanding of the mechanism of the RNA interference process would benefit drug design, the fight against disease, and the understanding of host defense mechanisms.

SUMMARY OF THE INVENTION

Ribonucleic acid interference molecules are provided. For example, in one aspect of the invention, a method for regulating gene expression comprises the following step. At least one nucleic acid molecule comprising at least one of one or more precursor sequences having SEQ ID NO: 1 through SEQ ID NO: 103,948, each one of the precursor sequences containing one or more mature sequences having SEQ ID NO: 103,949 through SEQ ID NO: 230,447, is used to regulate the expression of one or more genes.

It is to be understood that "SEQ ID NO." stands for sequence identification number. Each sequence identification number corresponds to a sequence stored in a text file on the accompanying Sequence Listing.

The method may further comprise inserting the at least one nucleic acid molecule into an environment where the at least one nucleic acid molecule can be produced biochemically. The method may further comprise inserting the at least one nucleic acid molecule in to an environment where the at least one nucleic acid molecule can be produced biochemically, giving rise to one or more interfering ribonucleic acids which affect one or more target sequences.

One or more of the sequences may be synthetically removed from the genome that contains them naturally. One or more of the sequences may be synthetically introduced in a genome that does not contain them naturally.

One or more target sequences may be encoded by the same genome as the one or more sequences. One or more target sequences may be encoded by a different genome from the one or more sequences. One or more target sequences are naturally occurring. One or more target sequences may be synthetically constructed.

One or more sequences may be transcribed, giving rise to one or more interfering ribonucleic acids which induce post-transcriptional repression of one or more target sequences. One or more sequences may be transcribed, giving rise to one or more interfering ribonucleic acids which induce gene silencing of one or more target sequences. One or more of the sequences may be synthetically constructed.

In a yet another aspect of the invention, at least one nucleic acid molecule comprises at least a portion of a precursor sequence having one of SEQ ID NO: 1 through SEQ ID NO: 103,948, wherein the portion comprises an amount of the sequence that does not significantly alter a behavior of the complete precursor sequence.

In a further aspect of the invention, at least one nucleic acid molecule comprises at least a portion of a mature sequence having one of SEQ ID NO: 103,949 through SEQ ID NO: 230,447, wherein the portion comprises an amount of the sequence that does not significantly alter a behavior of the complete mature sequence.

A more complete understanding of the present invention, as well as further features and advantages of the present invention, will be obtained by reference to the following detailed description.

DETAILED DESCRIPTION OF PREFERRED EMBODIMENTS

The teachings of the present invention relate to ribonucleic acid (RNA) molecules and their role in gene expression regulation. The term 'gene expression,' as used herein, refers generally to the transcription of messenger-RNA (mRNA) from a gene, and, e.g., its subsequent translation into a functional protein. One class of RNA molecules involved in gene expression regulation comprises microRNAs, which are endogenously encoded and regulate gene expression by either disrupting the translation processes or by degrading mRNA transcripts, e.g., inducing post-transcriptional repression of one or more target sequences. MicroRNAs are transcribed by RNA polymerase II as parts of longer primary transcripts known as pri-microRNAs. Pri-microRNAs are subsequently cleaved by Drosha, a double-stranded-RNA-specific ribonuclease, to form microRNA precursors or pre-microRNAs. Pre-microRNAs are exported by Exportin-5 from the nucleus into the cytoplasm where they are processed by Dicer. Dicer is a member of the RNase III family of nucleases that cleaves the pre-microRNA and forms a double-stranded RNA with overhangs at the 3' of both ends that are one to four nucleotides long. The mature microRNA is derived from either the leading or the lagging arm of the microRNA precursor. Finally, a helicase separates the double-stranded RNA species into single-stranded and the strand containing the mature microRNA becomes associated with an effector complex known as RISC (for RNA-induced silencing complex). The RISC+microRNA construct base pairs with its target in a sequence-specific manner using Watson-Crick pairing (and the occasional formation of G:U pairs). If the microRNA is loaded into an Argonaute-2 RISC, the target is cleaved at the binding site and degraded. In the presence of mismatches between a microRNA and its target, post-transcriptional gene silencing is effected through translational inhibition.

According to the teachings presented herein, the target sequence(s) may be naturally occurring. Alternatively, the target sequences may be synthetically constructed. A target sequence may be synthetically constructed so as to test prediction methods and/or to induce the RNAi/PTGS control of genes of interest. Additionally, a target sequence may be synthetically constructed so as to control multiple genes with a single RNA molecule, and also possibly to modify, in a combinatorial manner, the kinetics of the reaction by, for example, introducing multiple target sites. Similarly, the precursor sequence(s) may be either naturally occurring or synthetically constructed. For example, a precursor sequence of interest may be synthetically constructed and introduced into a cell that lacks that particular precursor. Further, when any of the above sequences are naturally occurring, they may be synthetically removed, for analysis purposes, from the genome that contains them, e.g., using standard molecular techniques.

As mentioned above, the present application is related to U.S. patent application entitled "System and Method for Identification of MicroRNA Target Sites and Corresponding Targeting MicroRNA," (Ser. No. 11/351,821), and to U.S. patent application entitled "System and Method for Identification of MicroRNA Precursor Sequences and Corresponding Mature MicroRNA Sequences from Genomic Sequences" (Ser. No. 11/351,951), both filed concurrently herewith, the disclosures of which are incorporated by reference herein.

In such related applications, several important questions are addressed. For example, for a given nucleotide sequence, is it part of or does it contain a microRNA precursor? Or, given the sequence of a microRNA precursor, where is the segment which will give rise to the mature microRNA? Further, is there more than one mature microRNA produced by a particular precursor, and if so, where are the segments which, after transcription, will give rise to these additional mature microRNAs? Another question addressed is the following: given the 3' untranslated region (3'UTR) of a given gene, which region(s) of it will function as a target(s) for some mature microRNA? This last question can also be asked when we are instead presented with the 5' untranslated region (5'UTR) or the amino acid coding region of a given gene. Also, for a given putative target site, which microRNA, if any, will bind to the putative target site?

For the purposes of this discussion, we only focus on the problem of whether a specific nucleotide sequence corresponds to a microRNA precursor or to a mature microRNA. A method for answering this question is described in the above referenced Ser. No. 11/351,951 patent application.

Summarily, the method comprises a first phase during which patterns are generated by processing an appropriate training set using a pattern discovery algorithm. If the training set comprises sequences of microRNA precursors, then the generated patterns, after appropriate attribute-based filtering, will be microRNA-precursor specific. If the training set comprises sequences of mature microRNAs, then the generated patterns, after appropriate attribute-based filtering, will be mature-microRNA specific. Alternatively, the training set can comprise putative mature microRNAs or putative microRNA precursors. In a preferred embodiment, two training sets were used, one comprising sequences of known microRNA precursors and one comprising sequences of known mature microRNAs.

The basic idea of this pattern-based method is to replace the training set of sequences with an "equivalent" representation that consists of patterns. The patterns can be derived using a pattern discovery algorithm, such as the Teiresias algorithm. See, for example, U.S. Pat. No. 6,108,666 issued to A. Floratos and I. Rigoutsos, entitled "Method and Apparatus for Pattern Discovery in 1-Dimensional Event Streams," the disclosure of which is incorporated by reference herein. The patterns are, ideally, maximal in composition and length (properties which are, by default, guaranteed by the Teiresias algorithm).

The generated microRNA-precursor-specific or mature-microRNA-specific patterns can then be used as predicates to identify, in a de novo manner, microRNA precursors from genomic sequence, or mature microRNAs in the sequence of a putative microRNA precursor. This is exploited in the method's second phase during which the patterns at hand are sought in the sequence under consideration: to determine whether a given nucleotide sequence S is part of, or encodes, a microRNA precursor the microRNA-precursor-specific patterns are used; and to determine whether a given nucleotide sequence S corresponds to, or contains a mature microRNA mature-microRNA-specific patterns are used.

In general, one anticipates numerous instances of microRNA-precursor-specific patterns in sequences that correspond to microRNA precursors whereas background and unrelated sequences should receive few or no such hits. If the number of pattern instances exceeds a predetermined threshold, then the corresponding segment of the sequence that receives the pattern support (and possibly an appropriately sized flanking region) is reported as a putative microRNA precursor. Analogous comments can be made about mature-microRNA-specific patterns and sequences containing mature microRNAs.

In the present application, pattern-discovery techniques, such as those described above, have been used in conjunction with recently released, publicly available genomic sequences to predict microRNA precursor and mature miRNA sequences related to the following organisms: *C. elegans* (Wormbase release 140); *D. melanogaster* (Berkely *Droso-*

*phila* Genome Project release 3.2); *M. musculus* (Ensembl assembly based on the NCBI 31 assembly); and *H. sapiens* (Ensembl assembly based on the NCBI 31 assembly). Namely, precursor sequences having SEQ ID NO: 1 through SEQ ID NO: 57,431 derived from the genome of *H. sapiens* are presented; precursor sequences having SEQ ID NO: 57,432 through SEQ ID NO: 101,967 derived from the genome of *M. musculus* are presented; precursor sequences having SEQ ID NO: 101,968 through SEQ ID NO: 103,203 derived from the genome of *D. melanogaster* are presented; precursor sequences having SEQ ID NO: 103,204 through SEQ ID NO: 103,948 derived from the genome of *C. elegans* are presented; mature sequences having SEQ ID NO: 103,949 through SEQ ID NO: 173,336 derived from the genome of *H. sapiens* are presented; mature sequences having SEQ ID NO: 173,337 through SEQ ID NO: 228,005 derived from the genome of *M. musculus* are presented; mature sequences having SEQ ID NO: 228,006 through SEQ ID NO: 229,484 derived from the genome of *D. melanogaster* are presented; and mature sequences having SEQ ID NO: 229,485 through SEQ ID NO: 230,447 derived from the genome of *C. elegans* are presented.

These predicted precursor and mature sequences are submitted herewith in electronic text format as 1500-565 DIV Sequence Listing.ST25 (including the same sequence listing as in the noted relation applications identified therein as the files ALL_MATURES.txt, created on Friday, Feb. 10, 2006, having a size of 11.4 Megabytes, and ALL_PRECURSORS.txt, Friday, Feb. 10, 2006, having a size of 14.5 Megabytes, on compact disc (CDROM)), the contents of which are incorporated by reference herein.

With respect to the sequences submitted herewith, for each precursor sequence that is listed, five features are presented (in addition to the sequence ID number and the corresponding organism name). One, the chromosome number (e.g., the chromosome identifier) is displayed. Two, the precursor start and end points on the corresponding chromosome are denoted. Three, the strand, either forward or reverse, on which the precursor will be found, is listed. Four, since the sequences displayed are predicted to fold into hairpin-like shapes, the predicted folding energy (also known as the energy required to denature the precursor) is presented. Five, each precursor sequence is presented.

As above, with respect to the sequences submitted herewith, for each mature sequence predicted, six features are presented (in addition to the sequence ID number and the corresponding organism name). One, as above, the chromosome number, (e.g., chromosome identifier) is displayed. Two, as above, the start and end points of the corresponding precursor sequence on the corresponding chromosome are denoted. Three, as above, the strand, either forward or reverse, on which the corresponding precursor will be found is listed. Four, as above, since the sequences displayed are derived from precursors which are predicted to fold into hairpin-like shapes, the folding energy of the corresponding precursor (also known as the energy required to denature the precursor) is presented. Five, the start and end points of the mature sequence on the corresponding chromosome are denoted. Six, each mature sequence is presented.

All of the sequences presented herein, whether precursors or matures, are deoxyribonucleic acid (DNA) sequences. One of ordinary skill in the art would easily be able to derive the RNA transcripts corresponding to these DNA sequences. As such, the RNA forms of these DNA sequences are considered to be within the scope of the present teachings. Also, it should be understood that the locations of the described sequences are given in the form of global coordinates, i.e., in terms of distances from the leftmost tip of the forward strand in the chromosome where the sequence at hand is located. In other words, all of the stated coordinates use the beginning of each chromosome's forward strand as a point of reference. If a sequence is reported to be on the reverse strand between locations X and Y, then one can actually generate the actual nucleotide sequence for it by excising the string contained between locations X and Y of the forward strand and then generating its reverse complement. These global coordinates are likely to change from one release of the genomic assembly to the next. Nonetheless, even though its actual location may change, the actual sequence that corresponds to a microRNA precursor or a mature microRNA is expected to remain unique and thus the corresponding sequence's new location will still be identifiable (except of course for the case where the sequence at hand corresponds to a segment that has been removed from the genomic assembly that is being examined).

One of ordinary skill in the art would also recognize that sequences that are either homologous or orthologous to the sequences presented herein, e.g., sequences that are related by vertical descent from a common ancestor or through other means (e.g., through horizontal gene transfer), will likely be present in genomes other than the ones mentioned herein. Such homologous/orthologous sequences are expected to generally differ from the sequences listed herein by only a small number of locations. Thus, the teachings presented herein should be construed as being broadly applicable to such homologous/orthologous sequences from species other than those listed above.

According to an exemplary embodiment, nucleic acid molecules may be generated based on the predicted precursor and mature sequences. The nucleic acid molecules generated may then be used to regulate gene expression. For example, as described generally above, mechanisms exist by which RNA molecules effect the expression of genes. By way of example only, the nucleic acid molecules generated may regulate the expression of a gene, or genes, by inducing post-transcriptional silencing of the gene, e.g. as described above. Using the predicted precursor and mature sequences to study gene expression may be conducted using techniques and procedures commonly known to those skilled in the art.

Although illustrative embodiments of the present invention have been described herein, it is to be understood that the invention is not limited to those precise embodiments, and that various other changes and modifications may be made by one skilled in the art without departing from the scope or spirit of the invention. For example, one may modify one or more of the described precursor sequences by adding or removing a number of nucleotides which is small enough to not significantly or radically alter the original sequence's behavior. The percentage of the resulting portion, with respect to the complete original sequence, that does not significantly alter such behavior depends on the sequence under consideration. Or one may insert one or more of the described mature sequences in an appropriately constructed "container sequence" (e.g., a precursor-like construct that is different than the precursor where this mature sequence naturally occurs) that still permits the excision of effectively the same mature sequence and thus the generation of an active molecule whose action is essentially unchanged with respect to that of the molecule corresponding to the starting mature sequence.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08445666B2). An electronic copy of the "Sequence Listing" will also be available from the USPTO upon request and payment of the fee set forth in 37 CFR 1.19(b)(3).

What is claimed is:

1. A method for post-transcriptionally repressing the expression of a target gene, the method comprising:
   inserting into the target gene a target sequence capable of specifically hybridizing with SEQ ID NO: 160280 or SEQ ID NO: 160281,
   allowing the target gene to be transcribed such that the transcript contains the target sequence capable of specifically hybridizing with SEQ ID NO: 160280 or SEQ ID NO: 160281,
   providing a nucleic acid molecule comprising a precursor sequence, SEQ ID NO: 46984, which precursor sequence comprises mature sequences SEQ ID NO: 160280 and SEQ ID NO: 160281, or providing a nucleic acid molecule comprising one or both of mature sequences SEQ ID NO: 160280 and SEQ ID NO: 160281, and
   allowing the precursor sequence or the nucleic acid comprising one or both mature sequences to be transcribed and processed to generate one or more interfering ribonucleic acids that comprise the RNA form of mature sequence SEQ ID NO: 160280 and/or the RNA form of mature sequence SEQ ID NO: 160281, such that the one or more interfering ribonucleic acid is present in the same environment as the transcript containing the target sequence, and the expression of the target gene is post-transcriptionally repressed.

2. The method of claim 1 wherein the method is performed in the presence of a genome that naturally contains the precursor sequence, SEQ ID NO: 46984, but from which the precursor sequence has been synthetically removed.

3. The method of claim 1 wherein the method is performed in the presence of a genome that does not naturally contain the precursor sequence, SEQ ID NO: 46984, but into which the precursor sequence has been synthetically introduced.

4. The method of claim 1 wherein the method is performed in the presence of a genome that encodes both the precursor sequence comprising the mature sequences and the target gene comprising the target sequence.

5. The method of claim 1 wherein the method is performed in the presence of two different genomes, wherein one genome encodes the precursor sequence comprising the mature sequences, and the other genome encodes the target gene comprising the target sequence.

6. The method of claim 1 wherein the precursor sequence comprising the mature sequences is synthetically constructed.

7. The method of claim 1, wherein the precursor sequence having SEQ ID NO: 46,984 is derived from a genomic sequence of *H. sapiens*.

8. The method of claim 1, wherein the mature sequences having SEQ ID NO: 160,280 and SEQ ID NO: 160,281 are derived from a genomic sequence of *H. sapiens*.

* * * * *